United States Patent [19]
Landis et al.

[11] Patent Number: 5,477,852
[45] Date of Patent: * Dec. 26, 1995

[54] NASAL POSITIVE AIRWAY PRESSURE APPARATUS AND METHOD

[75] Inventors: Robert M. Landis, Mountainside; Wayne W. Disanza, Toms River, both of N.J.

[73] Assignee: Airways Ltd., Inc., Matawan, N.J.

[ * ] Notice: The portion of the term of this patent subsequent to Feb. 17, 2013, has been disclaimed.

[21] Appl. No.: 155,479

[22] Filed: Nov. 19, 1993

Related U.S. Application Data

[63] Continuation-in-part of Ser. No. 19,993, Feb. 17, 1993, Pat. No. 5,269,296, which is a continuation of Ser. No. 784,371, Oct. 29, 1991, abandoned.

[51] Int. Cl.$^6$ .................................................. A61M 15/08
[52] U.S. Cl. ............................. 128/207.18; 128/207.15; 128/204.18; 606/192; 604/94
[58] Field of Search ......................... 128/207.15, 207.18, 128/DIG. 26, 911, 912, 207.16, 207.17, 204.11, 204.12, 204.18, 200.24, 200.26, 201.22, 203.21, 205.25; 606/191, 192, 196; 604/94

[56] References Cited

U.S. PATENT DOCUMENTS

| | | | |
|---|---|---|---|
| 812,706 | 2/1906 | Warbasse | 128/207.13 |
| 1,158,780 | 11/1915 | Bolton | 128/207.13 |
| 1,176,886 | 3/1916 | Ermold | 128/207.13 |

(List continued on next page.)

FOREIGN PATENT DOCUMENTS

| | | | |
|---|---|---|---|
| 4010975 | 10/1991 | Germany | 606/196 |
| 220978 | 6/1968 | Sweden | 606/196 |
| 1250307 | 8/1986 | U.S.S.R. | 128/207.18 |
| 1255128 | 9/1986 | U.S.S.R. | 128/207.18 |
| WO8203548 | 10/1982 | WIPO . | |
| 9220392 | 11/1992 | WIPO . | |

OTHER PUBLICATIONS

"Management of Chronic Alveolar Hyperventilation with Nasal Positive Pressure Breathing," DiMarco, et al: Chest: 92/5/952–954 Nov. 1987.

Benefit of Nasal CPAP in Obstructive Sleep Apnea is Due to Positive Pharyngeal Pressure N. C. Abbey; K. R. Cooper and J. A. Kwentus, Sleep 12(5) 420–422 (1989).

Long–Term Compliance with Nasal Continuous Positive Airway Pressure Therapy of Obstructive Sleep Apnea; R. E. Waldhorn, T. W. Herrick, M. C. Nguyen, A. E. O'Donnell, J. Sodero, and S. J. Potolicchio; Chest 1990: 97; 33–38.

Obstructive Sleep Apnea Treated by Independently Adjusted Inspiratory and Expiratory Positive Airway Pressures via Nasal Mask; M. H. Sanders, N. Kern; Chest 1990; 98:317–24.

Surgical Treatment of Obstructive Sleep Apnea: Is Mandibular Surgery an Advance? Chest 1990; 98:1315–16.

(List continued on next page.)

*Primary Examiner*—Edgar S. Burr
*Assistant Examiner*—Eric P. Raciti

[57] ABSTRACT

A nasal positive airway pressure device is provided having a pair of nasal members each having a cannula tip to be inserted into the nares of the patient. Each cannula is tapered from a substantially circular cross-section outside the patient's nostril to a substantially oval cross-section at the tip inserted into the nostril. An inflatable cuff surrounds each cannula with the interior space of the cuff communicating with the lumen of the cannula through at least one aperture in the side wall of the cannula. The nasal members are connected to one or more flexible hoses which, in turn, are connected to a source of positive air pressure. In use, positive air pressure is supplied to the each cannula tip through the air hoses and nasal members. The positive air pressure inflates the cuffs to hold the nasal members in place and to effect treatment, The tapered tip configuration, soft inflatable cuffs and adjustable positioning of the nasal members and tip provide a device which is more comfortable to the user. A variable diameter orifice for nasal positive airway pressure treatment is also contemplated.

28 Claims, 10 Drawing Sheets

U.S. PATENT DOCUMENTS

| | | | |
|---|---|---|---|
| 1,206,045 | 11/1916 | Smith | 128/206.24 |
| 1,632,449 | 6/1927 | McKesson | 128/206.24 |
| 2,185,997 | 1/1940 | Heidbrink | 128/204.29 |
| 2,245,969 | 6/1941 | Francisco | 128/207.18 |
| 2,259,817 | 10/1941 | Hawkins | 128/207.18 |
| 2,493,326 | 1/1950 | Trinder | 606/196 |
| 2,931,358 | 4/1960 | Sheridan | 128/207.18 |
| 3,481,339 | 12/1969 | Puig | 128/207.15 |
| 3,516,407 | 6/1970 | Ruggero | 128/200.28 |
| 3,566,862 | 3/1971 | Schuh | 128/207.18 X |
| 3,568,678 | 3/1971 | Pourquier | 128/207.18 |
| 3,640,282 | 2/1972 | Kamen | 128/207.15 |
| 3,683,907 | 8/1972 | Cotabish | 128/200.28 |
| 3,707,151 | 12/1972 | Jackson | 128/207.15 |
| 3,766,924 | 10/1973 | Pidgeon | 606/196 |
| 3,794,036 | 2/1974 | Carroll | 128/207.15 |
| 3,850,176 | 11/1974 | Gottschalk | 606/196 |
| 3,856,051 | 12/1974 | Bain | 138/114 |
| 3,903,893 | 9/1975 | Scheer | 606/196 |
| 4,056,104 | 11/1977 | Jaffe | 128/207.15 |
| 4,090,518 | 5/1978 | Elam | 128/207.15 |
| 4,106,505 | 8/1978 | Salter | 128/207.18 |
| 4,151,843 | 5/1979 | Brekke | 128/205.25 |
| 4,156,426 | 5/1979 | Gold | 128/207.18 |
| 4,178,937 | 12/1979 | Taylor | 604/103 |
| 4,216,769 | 8/1980 | Grimes | 128/207.13 |
| 4,235,239 | 11/1980 | Elam | 128/207.15 |
| 4,273,124 | 6/1981 | Zimmerman | 128/207.18 |
| 4,367,735 | 1/1983 | Dali | 128/207.18 |
| 4,422,456 | 12/1983 | Tiep | 128/207.18 |
| 4,465,067 | 8/1984 | Koch | 128/207.18 |
| 4,538,606 | 9/1985 | Whited | 128/207.15 |
| 4,655,213 | 4/1987 | Rapoport et al. | 128/205.25 |
| 4,753,233 | 6/1988 | Grimes | 128/207.18 |
| 4,782,832 | 11/1988 | Trimble | 128/207.18 |
| 4,790,308 | 12/1988 | Weichselbaum | 128/207.18 |
| 4,818,320 | 4/1989 | Weichselbaum | 156/227 |
| 4,836,200 | 6/1989 | Clark | 128/207.18 |
| 4,915,105 | 4/1990 | Lee | 128/205.27 |
| 5,024,220 | 6/1991 | Holmgreen et al. | 128/207.18 |
| 5,042,478 | 8/1991 | Kopala | 128/207.18 |
| 5,065,756 | 11/1991 | Rapoport | 128/204.18 |
| 5,105,807 | 4/1992 | Kahn et al. | 128/207.18 |
| 5,139,510 | 8/1992 | Goldsmith, III et al. | 606/196 |
| 5,148,802 | 9/1992 | Sanders et al. | 128/204.18 |
| 5,161,525 | 11/1992 | Kimm et al. | 128/204.26 |
| 5,199,424 | 4/1993 | Sullivan et al. | 128/204.18 |
| 5,245,995 | 9/1993 | Sullivan et al. | 128/204.23 |
| 5,269,296 | 12/1993 | Landis | 128/207.18 |

OTHER PUBLICATIONS

Maxillofacial Surgery and Nasal CPAP: A Comparison of Treatment for Obstructive Sleep Apnea Syndrome; R. W. Riley, N. B. Powell and C. Guilleminault Chest 1990; 98:1421–25.

The Effect of Nightly Nasal CPAP Treatment on Underlying Obstructive Sleep Apnea and Pharyngeal Size; N. A. Collop, A. J. Block, and D. Hellard; Chest 1991; 99:855–60.

The Effect of Positive Reinforcement on Hourly Compliance in Nasal Continuous Positive Airway Pressure Users with Obstructive Sleep Apnea, E. C. Fletcher and R. A. Luckett; Am. Rev. Respir. Dis. 1991; 143:936–941.

Nasal Continuous Positive Airway Pressure Facilitates Respiratory Muscle Function During Sleep in Severe Chronic Obstructive Pulmonary Disease, B. J. Petrof, R. J. Kimoff, R. D. Levy, M. G. Cosio, and S. B. Gottfried; Am. Rev. Respir. Dis. 1991; 143:928–935.

Efficacy of Nocturnal Nasal Ventilation in Patients with Restrictive Thoracic Disease, N. S. Hill, S. E. Eveloff, C. C. Carlisle and S. G. Goff Am. Rev. Respir. Dis. 1992; 145:365–371.

Nocturnal Nasal Intermittent Positive Pressure Ventilation with Bi–Level Positive Airway Pressure (BiPAP) in Respiratory Failure, R. E. Waldhorn; Chest 1992; 101:516–521.

Physiologic Evaluation of Pressure Support Ventilation by Nasal Mask in Patients with Stable COPD, Chest 1992; 101:385–91.

"Softwear™ Nasal Mask" Lifecare ©1991.

New Product News—Companion 318 Nasal CPAP System from Puritan–Bennett.

Harmonization and the Work of Breathing: For Bi–Level Respiratory Therapy; Puritan–Bennett.

Companion$^R$ Adam Nasal CPAP Circuit.

New Mask Fitting Program for Health Care Professionals; Night Times, Jun. 1993.

The BiPAP® System Compensates for Leaks, Respironics, Inc. ©1993.

Why Mask Leaks Are No Longer A Problem, Respironics, Inc. ©1993.

NASAL POSITIVE AIRWAY PRESSURE APPARATUS AND METHOD

The present application is a continuation-in-part of U.S. patent application Ser. No. 08/019,993, filed Feb. 17, 1993, now U.S. Pat. No. 5,269,296, issued Dec. 14, 1993, a continuation of U.S. patent application Ser. No. 07/784,371, filed Oct. 29, 1991, now abandoned.

TECHNICAL FIELD

The present invention relates to an apparatus and method for treating sleep apnea. More specifically, the present invention provides a nasal positive airway pressure device which is reliable and comfortable to wear and, consequently, more acceptable to the patient. Methods of making and using the device are also disclosed.

BACKGROUND OF THE INVENTION

Obstructive sleep apnea is a condition in which the patient's airway passage is blocked and no air can pass to the lungs during sleep. During a customary sleep period a person suffering from sleep apnea can experience so-called apneic events. Apneic events are periods when the patient's airway becomes blocked, often for ten seconds or more, until the patient rouses from sleep and starts breathing normally again. Those suffering from sleep apnea may experience numerous apneatic events each night, causing a deficiency of restful sleep and, due to depleted oxygen levels, possible long term health problems such as heart ailments.

Continuous positive airway pressure (CPAP) and, more specifically, nasal continuous positive airway pressure (nCPAP) has been shown to be an effective treatment for sleep apnea. See "Benefit of Nasal CPAP in Obstructive Sleep Apnea is Due to Positive Pharyngeal Pressure", N. C. Abbey, K. R. Cooper and J. A. Kwentus, Sleep 1989, 12: (5):420–422; "The Effect of Nightly Nasal CPAP Treatment on Underlying Obstructive Sleep Apnea and Pharyngeal Size", N. A. Collopp. A. J. Block and D. Hetlard, Chest 1991, 99:855–860; and "Nasal Continuous Positive Airway Pressure Facilitates Respiratory Muscle Function During Sleep in Severe Chronic Obstructive Pulmonary Disease", B. J. Petrof, R. J. Kimoff, R. D. Levy, M. G. Cosoi and S. B. Gottfried, Am. Rev. Respir. Dis. 1991; 143:928–935. This treatment involves applying a constant supply of gas, typically a mixture of air supplemented with moisture vapor or oxygen, to the nasal passages at a predetermined, slightly elevated pressure in order to prevent negative pressure conditions within the passageway.

More recently, a related form of treatment has been tested and may achieve success similar to nCPAP. In this treatment, known as BiPAP™ therapy, a controller regulates the gas pressure in response to the patient's breathing patterns and supplies positive gas pressure at a first gas pressure during the inspiratory phase, i.e., inhalation by the patient, and supplies gas at a second, reduced pressure during the expiratory phase, i.e., as the patient exhales. The first gas pressure typically corresponds to pressure used in nCPAP treatment and is on the order of about 10 centimeters of water or greater. The second pressure level is about half the first gas pressure, and typically is about 5 to 7 centimeters of water pressure. It has been reported that reducing the gas pressure during exhalation provides increased patient comfort and compliance by reducing the work done by the patient in overcoming the gas pressure during exhalation. BiPAP™ treatment is disclosed in "Obstructive Sleep Apnea Treated by Independently Adjusted Inspiratory and Expiratory Positive Airway Pressures via Nasal Mask", M. H. Sanders and N. Kern,.Chest 1990; 98:317–24; "Nocturnal Nasal Intermittent Positive Pressure Ventilation with Bilevel Positive Airway Pressure (BiPAP) in Respiratory Failure", R. E. Waldhorn, Chest 1992, 101:16–52; "Efficacy of Nocturnal Nasal in Patients with Restrictive Thoracic Disease", Am. Rev. Respir. Disease, 1992; 145:365–371; "Physiologic Evaluation of Pressure Support Ventilation by nasal mask in Patients With Stable COPD", N. Ambrosino, S. Nava, P Bertone, C. Frachia, C. Rampulla, Chest 1992; 101:385–91.

In general, nCPAP and BiPAP™ treatment typically involve placing a mask over the nose of the patient by means of a harness or other headgear and providing a source of positive low pressure air connected to the mask. Conventional nasal masks are considered uncomfortable, cumbersome and noisy (due to air leaks) and in many cases are a formidable obstacle to patient acceptance of nCPAP or BiPAP™ therapy.

U.S. Pat. No. 4,782,832 issued to Trimble, et. al. proposes a device for nCPAP treatment intended to overcome the deficiencies of conventional mask devices. The Trimble structure has become the accepted apparatus for nCPAP treatment. Trimble discloses a nasal puff adapted to be worn adjacent the nose of the wearer-patient. The nasal device includes a relatively small plenum chamber including structure defining an inlet adapted for coupling with a source of gas, and a pair of spaced apart, separate gas outlets in communication with the inlet. Typically, the plenum chamber is in the form of a generally Y-shaped hollow body with the gas outlets located in the branches of the body. The nasal puff further includes a pair of gas delivery elements each having a gas flow passageway therethrough and respectively operatively coupled with a corresponding gas outlet for conveying gas from the outlet through and out the passageway. Each of the gas delivery elements is configured for insertion into a respective nares of a patient, and for this purpose the outer wall of the elements are generally frusto-conically shaped so as to sealingly engage the nares-defining surfaces of the nose. Adjustability of the nares elements is provided by rotatably mounting the elements to the plenum housing and by mounting the elements in slots permitting selective lateral positioning of the elements with respect to each other. Flexible bellows-type corrugated sections can be provided in each of the elements and/or in appropriate positions in the plenum housing so as to add further ranges of flexibility and adjustability. The nares elements are fabricated from relatively soft, deformable, shape-retaining synthetic resin material permitting manual deformation and alteration of the effective shape and position of the elements. Trimble discloses a harness to be worn on a patient's head with flexible mask-retaining straps extending from the main harness strap to each side of the nasal puff. The harness assembly includes an elongated gas;conveying tube which is adapted for coupling with the inlet of the nasal puff and extends upwardly along the length of the bridge of the patient's nose and across the patient's forehead, terminating at the top of the patient's forehead. The tube is longitudinally bifurcated to divide the overall tube and present a pair of elongated, juxtaposed passageways, one of which is connected to a source of pressurized air and the other to a discharge tube for purging patient-generated $CO_2$ during exhalation). In an alternative embodiment Trimble discloses inflatable nares elements that are inserted into the nares and inflated manually by a separate source of pressure.

The Trimble nasal puff and harness assembly is an accepted apparatus for treatment of sleep apnea using nCPAP therapy. While the Trimble device is an improvement over prior mask structures, some patients continue to object to the Trimble structure as uncomfortable to wear. Studies show that a small but significant number of patients fail or are unable to continue nCPAP treatment due in at least some cases to the inconvenience or discomfort of wearing the presently available apparatus. See "The Effect of Positive Reinforcement on Hourly Compliance in Nasal Continuous Positive Airway Pressure Users with Obstructive Sleep Apnea", E. C. Fletcher and R. A. Luckett, Am. Rev. Respir. Dis. 1991; 143:936–941; "Maxillofacial Surgery and Nasal CPAP", R. W. Riley, N. B. Powell, C. Guilleminault, Chest 1990; 98:1421–1425; and "Surgical Treatment of Obstructive Sleep Apnea—Is Mandibular Surgery an Advance?", Chest 1990; 98:1315–1316.

Notwithstanding the general consensus that nasal positive airway pressure is an effective treatment for sleep apnea, a substantial number of patients either cannot tolerate treatment or choose to forego treatment. It is believed a substantial number of such patients could benefit from a nasal positive airway pressure apparatus which is more convenient to use and comfortable to wear, thereby resulting in increased treatment compliance. The device disclosed and claimed herein may find application to either nCPAP or BiPAP treatment.

SUMMARY OF THE INVENTION

In accordance with the present invention, a positive nasal airway pressure device is provided for treatment of sleep apnea. The device includes means for securing the device to the patient's head, i.e., a head strap or harness, a primary air tube to be connected to a source of air pressure in a known manner, at least one connector hose and a pair of nasal members connected to the at least one connector hose. The nasal members are connected to the connector hose. Preferably, the at least one connector hose comprises a pair of flexible hoses, which may be corrugated to enhance adjustability, and each nasal member is connected to one connector hose.

In a first embodiment of the invention the nasal member is a substantially U-shaped hollow body connected to the connector hose. The nasal member tapers to a substantially oval cross-section at the end distal to the connector hose. The nasal member includes an aperture in the sidewall of the member and an inflatable cuff surrounding the nasal member and overlying the aperture.

In a second embodiment of the invention the nasal member is a substantially rigid U-shaped hollow piece having a substantially circular cross-section throughout its length connected at one end to the connector hose and at the other to a tip member. The tip member is hollow and has a substantially circular cross-section at the end thereof connected to the nasal member. The tip member preferably tapers to a substantially oval cross-section at the opposite end to be inserted into the patient's nostril. The tip member may be friction fit to the nasal member and preferably is rotatably connected to the nasal member to facilitate adjustability. The tip includes an aperture through the side wall and an inflatable cuff surrounding at least a portion of the tip and overlying the aperture so that the interior space of the inflatable cuff communicates with the hollow interior of the tip. Preferably, the inflatable cuff extends to the end of the tip member and slightly beyond the end of the tip.

In use, the device is secured to the head of the user with the securing strap or harness. The flexible connector hoses are adjusted, as necessary, to position the nasal members for insertion into the patient's nares. Because the connector hoses are flexible the position of the nasal members may be adjusted by moving the hoses away from one another. If the hoses are corrugated the length of each hose also may be adjusted independent of the other. The nasal tip members further may be adjusted by rotating the tips relative to the nasal members so that the oval tip is aligned with the physiological opening of the nostril. The tip may then be inserted into the nostril and the source of pressurized air activated to supply pressurized air to the tip via the primary tube, connector hoses and nasal members. The pressurized air enters the patient's nostril through the hollow nasal tip member to effect treatment. In addition, the pressurized air enters the inflatable cuff through the aperture to inflate the cuff so that the cuff engages the nares walls to hold the tip members in place within the nares. In the preferred embodiment wherein the cuff extends slightly beyond the end of the tip member, the cuff additionally protects the sensitive nare walls from abrasion due to contact with the end of the tip. During the inspiratory phase, i.e., inhalation, the pressure from the source of pressurized air maintains the cuff inflated and effects treatment. During the expiratory phase, i.e., exhalation, excess pressure is vented through vent holes on the nasal member and the exhaled pressurized air maintains the cuffs in their inflated state. Because the tip is tapered to conform to the shape of the nostril opening and because only the soft flexible cuff member contacts the nares walls, the tip in accordance with the preferred embodiment of the invention is much more comfortable than prior art devices. Further, the rotational adjustability of the tip relative to the nasal member and the independent adjustability of the position of the tip members relative to one another by adjusting the air connectors makes the present invention more convenient to use.

A further aspect of the invention relates to the fabrication of the inflatable cuffs. In a preferred mode of making the cuffs, a thermoplastic tube such as polyurethane is inserted into a hollow mandrel and expanded under heat and pressure to conform to the shape of the mandrel. The inflated portion is cut free from the tube and one end of the thus formed cuff is placed over and cemented to the distal oval end of the tip member. With the first end of the secured to the tip member, the cuff is everted and folded over the tip and secured to the body of the tip member so that the cuff extends slightly beyond the distal tip of the tip member, surrounds at least a portion of the tip member, and overlies the aperture.

The apparatus in accordance with the invention provides considerable advantages over existing treatment devices by providing a device which is easier to adjust and more comfortable to wear. These and other advantages of the invention will become apparent to those skilled in the art from the foregoing general description and the following detailed disclosure, and from practice with the invention.

BRIEF DESCRIPTION OF THE DRAWINGS

The present invention and the disclosure set forth herein can be better understood with reference to the accompanying drawings, which form a part of the disclosure, in which.

Figure 1:
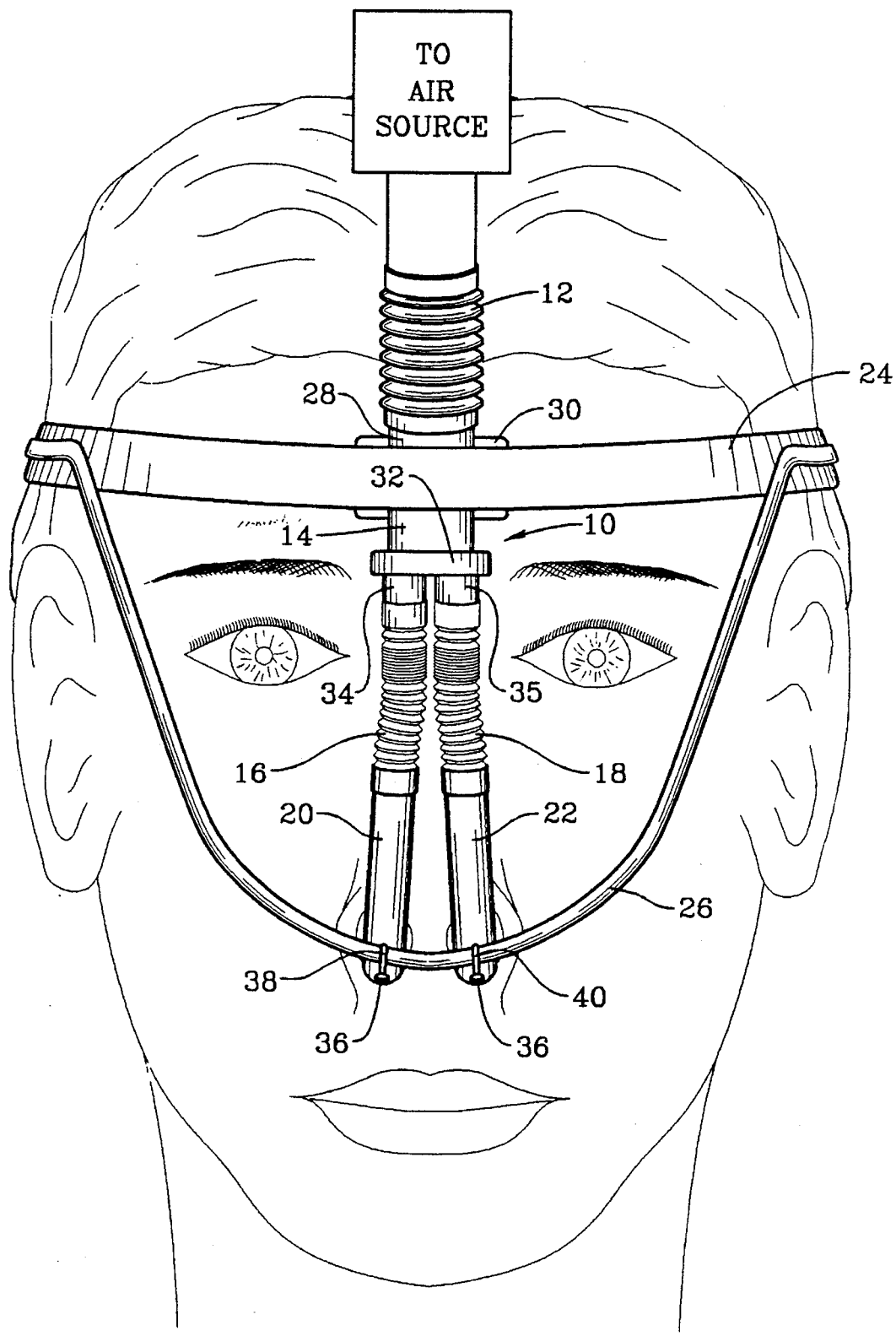
FIG. 1 is a front elevation view of the apparatus in accordance with the invention mounted upon the head of a patient.

As those skilled in the art will appreciate, the foregoing drawings are illustrative only, and show the features of the invention in accordance with the invention as they relate to one another. The drawings are not drawn strictly to scale and should be interpreted accordingly.

DETAILED DESCRIPTION OF THE PREFERRED EMBODIMENTS

Referring now to the drawings, there is shown a nasal positive airway pressure device 10 in accordance with the invention. Device 10 generally consists of a primary tube 12, a connector piece 14, and a pair of nasal tubes 16, 18 each connected to a nasal member 20, 22. The apparatus may be secured to the head of the user with a head band 24 in a known manner. An adjustable support strap 26 preferably extends from the head band to aid in holding the nasal members adjacent the nose of the user. At least a portion of each nasal member 20, 22 defines a cannula configured and dimensioned to fit within the nares of a patient. Inflatable cuffs (see FIGS. 3 and 4) surround at least a portion of each cannula to hold the cannula in position within the patient's nares in a manner to be explained below. Each nasal cannula preferably is substantially oval or elliptical in cross-section at the open tip thereof distal to nasal tube members 16, 18, and gradually tapers to a substantially circular cross-section outside the patient's nares. The inflatable cuff surrounding each cannula is made of a relatively inelastic plastic material, and the interior space of the cuff communicates with the lumen of the cannula through an aperture in the cannula wall. As will be explained in greater detail below, the oval tip cross-section of the cannula in accordance with the invention provides greater patient comfort. In addition, the inflatable cuffs inflate under pressure during nCPAP or BiPAP treatment to hold the cannula within the nares in a manner which is more comfortable to the user than prior treatment devices.

The invention provides a positive airway pressure device which is easily secured to the head of a user and adjusted for maximum comfort to the user, a significant advantage over existing treatment devices.

Referring now to FIG. 1, a front elevation view of a positive airway pressure device constructed in accordance with the invention mounted to the head of a user, primary tube 12 is made of a relatively flexible adjustable material, such as plastic, and is connected to a source of pressurized gas (not shown). The source of pressurized gas may be any source suitable for treating sleep apnea, and may be a source of pressurize air with or without supplements such as oxygen. The source of gas may provide continuous pressure as used in nCPAP treatment, or may provide varied levels of pressure such as used in BiPAP™ treatment. In either case, the gas pressure typically is in the range of about 5 to about 15 centimeters of water. As shown in FIG. 1, primary tube 12 may be corrugated in whole or in part to facilitate adjustment. Primary tube 12 typically would have an outer diameter of about 0.25 to 0.375 inches with an inner diameter of about 0.25 inches.

Referring again to FIG. 1, primary tube 12 is attached to connector 14 at a substantially cylindrical section 28 of connector 14. Primary tube 12 may be connected to cylindrical section 28 in any convenient manner suitable for coupling without substantial loss of gas pressure, such as by friction fit, gluing, welding, threading, bayonet mount or the like. Cylindrical section 28 is placed under head band 24 to hold the device in place relative to the user's head. Preferably, a foam pad 30 is placed between the cylindrical section and the forehead of the user for added comfort. As will be appreciated, foam pad 30 may be pre-attached to connector 14 for ease of use. Headband 24 preferably is a cloth or plastic strap with a simple fastening structure such as a hook and loop fastener, e.g., a Velcro™ fastener. Connector 14 further includes a chamber portion 32 having a pair of nasal tube connectors 34, 35 extending therefrom and adapted to be connected to nasal tubes 16, 18. As shown, connector 14 preferably is positioned adjacent the ferehead of the user. Connector 14 preferably is made of a substantially rigid material, such as rigid plastic or metal. Suitable plastics include homopolymers, copolymers, blends and mixtures of polystyrene, ABS, polycarbonate, acrylics, polyethylene, polyethylene terathalate, polybutylene, polybutylene terathalate and others, Suitable metals include stainless steel, titanium, aluminum and alloys thereof. As shown, nasal tubes 16, 18 are connected to nasal tube connectors 34, 35 so as to maintain gas pressure, such as by friction or snap fit, gluing, welding, etc. Preferably, nasal tube connectors 34, 35 are spaced apart by a center-to-center distance approximating the center-to-center distance between the nares of an average user, such as about one(1) centimeter. As will be explained below, spacing the nasal tube connectors by this distance facilitates adjustment of the device for optimal patient comfort. Nasal tubes 16, 18 preferably are made of a flexible plastic material, and may be made of corrugated expandable plastic tubing made from polypropylene provided in a compact state to be expanded by the user for adjustment of the device. The proximal ends of nasal tubes 16, 18 are connected to nasal tube connectors 34, 35, respectively. The distal ends of nasal tubes 16, 18 are connected to nasal members also in a manner to preserve gas pressure, such as by friction or snap fit, gluing, welding, etc.

Figure 2:
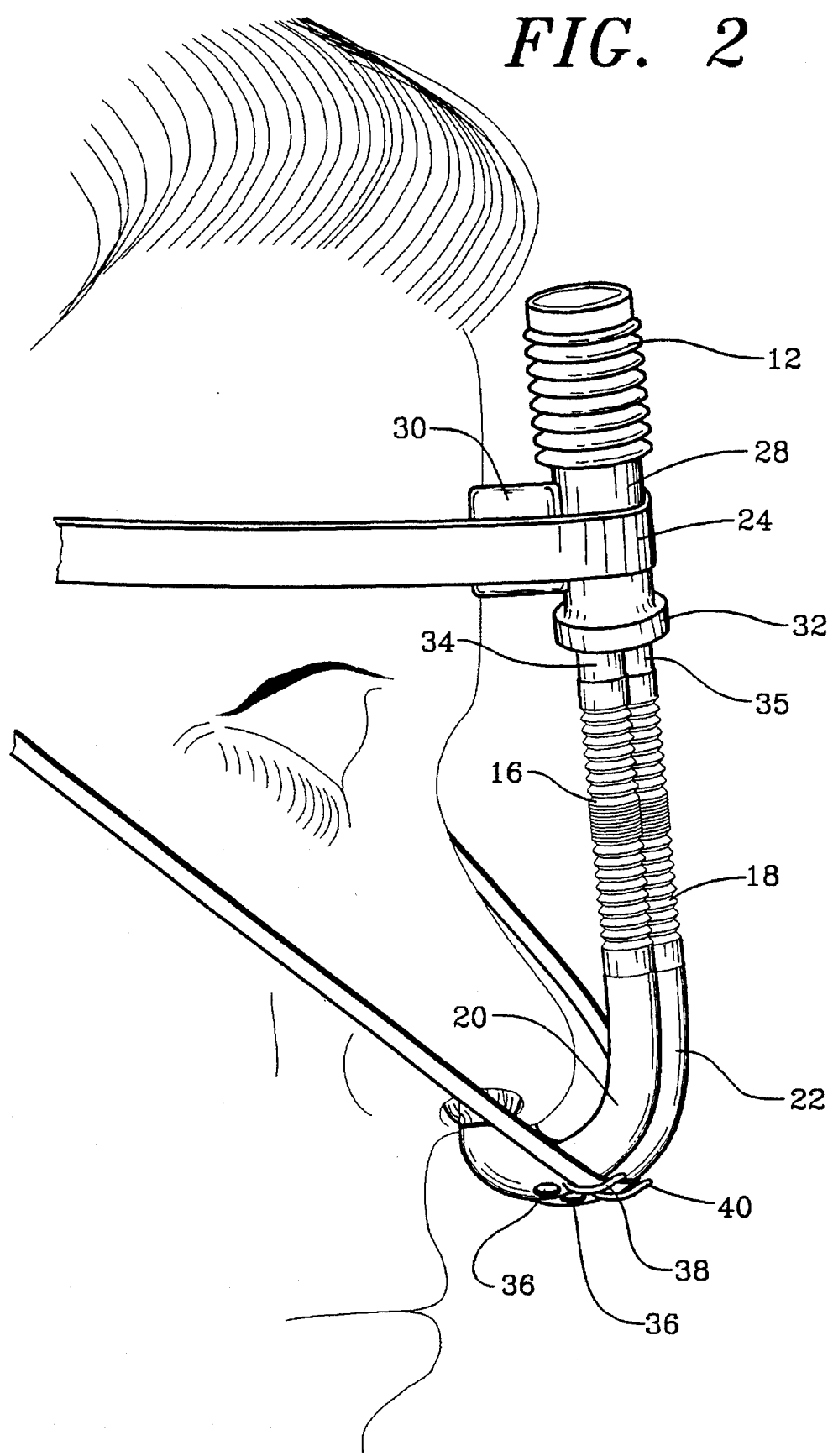
FIG. 2 is a side view of the apparatus shown in FIG. 1.

Referring now to FIG. 2, nasal members 20, 22 are curved pieces having a substantially U-shape to conform to the facial anatomy. One end of each curved nasal member is connected to nasal tubes 16, 18, with the other end of the U-shaped pieces having a tip configured, dimensioned and angled to be comfortably inserted into the user's nostrils. Nasal members 20, 22 also have vent holes 36 through a portion thereof as well as strap-receiving hook members 38, 40 adapted to receive a portion of a strap 42 to further support the nasal members in the nares of the patient (also see FIG. 1). As shown, strap 42 is adjustably secured to headband 24, such as by hook and loop fasteners.

Figure 3:
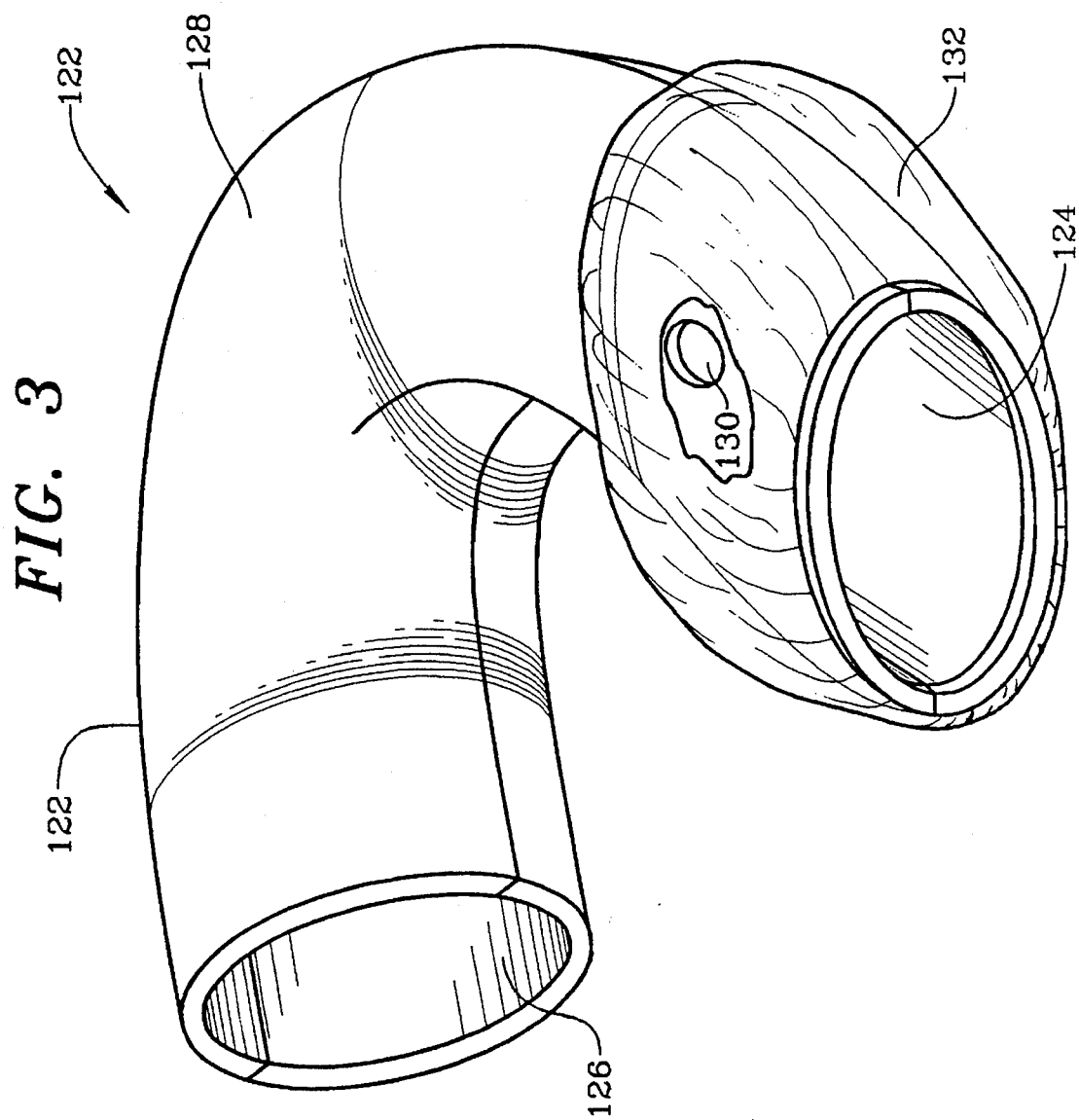
FIG. 3 is a perspective view of a nasal tip member in accordance with a first embodiment of the invention with an inflatable cuff attached to the tip member in partial cutaway view.

In a first embodiment of the invention shown in FIG. 3, nasal members 20, 22 each comprise an integral curved hollow nasal member unit 122 having a distal open end 124 of substantially oval cross-section configured and dimensioned for insertion into a patient's nares. Nasal member 122 has a proximal open end 126 of substantially circular cross-section, and a body section 128 between the first and second open ends. Body section 128 tapers from the oval cross-section of the distal end to the circular cross-section of the proximal open end. Adjacent distal end 124 is an aperture 130 through the sidewall defining the nasal member, and an inflatable cuff 132 secured to the outer surface of the nasal member to surround a portion of the nasal member and overlie the aperture. Cuff 132 is shown in an inflated condition in FIG. 3. The air space inside cuff 132 communicates through aperture 130 with the air space within the lumen of nasal member 122. Preferably, the distal open end of the nasal member defines an oval opening having a major diameter of about 0.3 to about 0.4 inches and a minor diameter of about 0.2 to about 0.3 inches. Nasal member 122 is substantially rigid, and may be made from any suitable biocompatible material, such as metal or plastic. Suitable metals include stainless steel, titanium, aluminum and alloys thereof. Suitable plastics include homopolymers, copolymers, blends and mixtures of polystyrene, ABS, polycarbonate, acrylics, polyethylene, polyethylene terathalate, polybutylene, potybutylene terathalate and others. The thickness of the nasal member side wall may be about 0.05 to about 0.07 inches. Inflatable cuff 132 preferably is made from a substantially inelastic, non-irritating, soft plastic material such as polyurethane. Other suitable plastics include polyvinyl chloride (PVC).

Figure 4:
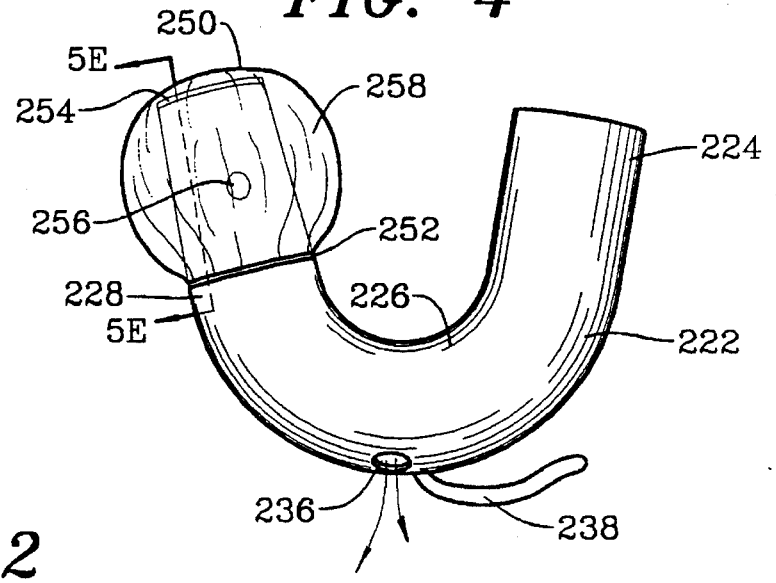
FIG. 4 is a side view of a nasal tip member in accordance with a second embodiment of the invention with an inflatable cuff shown attached to the nasal tip member in the inflated condition.

In a second embodiment of the invention the nasal member is constructed with a separate removable tip as shown in FIGS. 4 and 5A–5E and 12. As there shown, nasal member 222 has a proximal nasal tube receiving section 224, a curved body section 226 and a distal tip engaging end 228. Consistent with FIGS. 1 and 2, nasal member 222 includes at least one vent hole 236 and strap retaining hook 238. Nasal tip 250 is connected to nasal member 222 at nasal member end 228. Nasal tip 250 has a first, proximal end 252 to engage and be connected to nasal member 222, such as by friction fit or other suitable removable attachment, and a second, distal open end 254. Tip 250 includes at least one aperture 256 through a sidewall thereof intermediate the first and second ends and an inflatable cuff 258 surrounding at least a portion of the tip member overlying and enclosing aperture 256. In FIG. 4, tip member 250 is shown mounted to nasal member 222 with inflatable cuff 258 in an inflated condition. As explained in greater detail below, tip 250 and inflatable cuff 258 are configured and dimensioned to be inserted into a patient's nares in the manner illustrated in FIGS. 1–2. In FIG. 4, tip 250 and tip aperture 256 are visible through a transparent cuff 258. Of course, cuff 258 may also be opaque or pigmented to a particular color, if desired. As also shown in FIG. 4, inflated cuff 258 extends slightly beyond distal open end 254 of the tip. In this embodiment, nasal member 222 is of substantially circular cross-section over its entire length for ease of manufacture and attachment to the nasal tubes and tip members. Tip member 250 is of substantially circular cross-section at the proximal end attached to the nasal member, and tapers to a substantially oval cross-section at the distal end thereof. As will be appreciated, a circular cross-section at the connection of tip 250 to nasal member 222 facilitates a rotatable connection. Independent rotation of tips 250 allows the tips to rotate substantially about the axis of nasal member end 228 and, hence, the patient's nares to rotationally align the oval opening with the nasal opening.

Figure 5E:
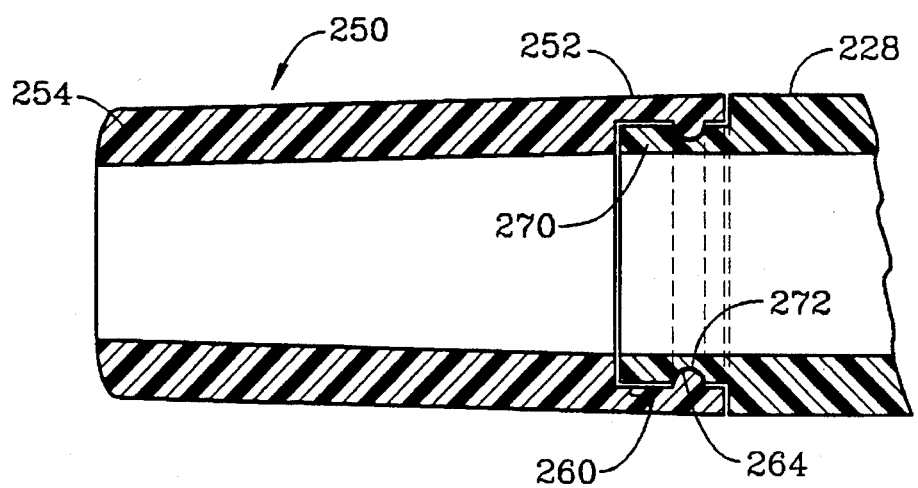
FIG. 5E is a partial cross-section view of the nasal tip member of FIG. 5A illustrating in detail the area of snap fit connection to the nasal tube member.
Figure 5B:
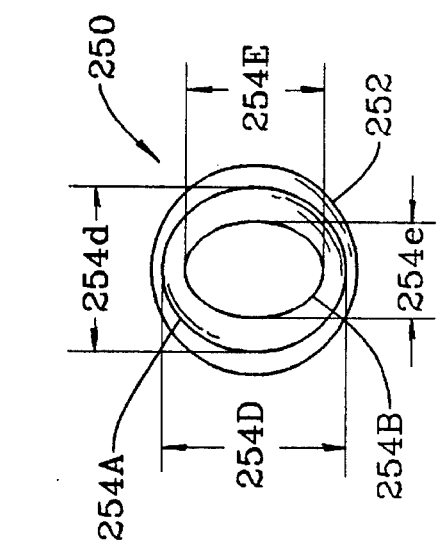
FIG. 5B is a distal end view of the tip member shown in FIG. 5A.
Figure 5D:
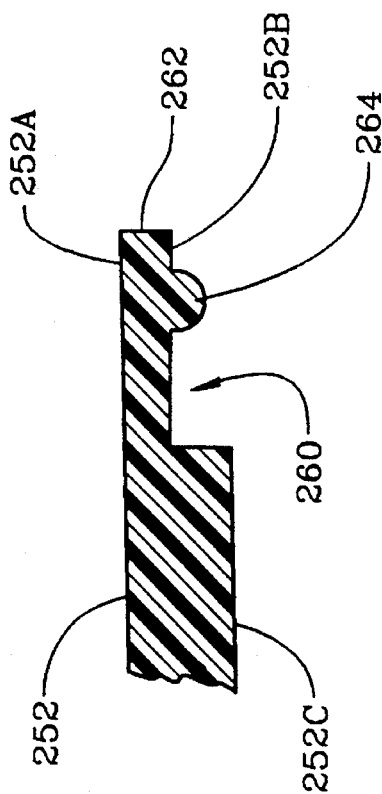
FIG. 5D is a side cross-section view of the tip member of FIG. 5A, illustrating a snap fit connection between the nasal tip member and a nasal tube.
Figure 5A:
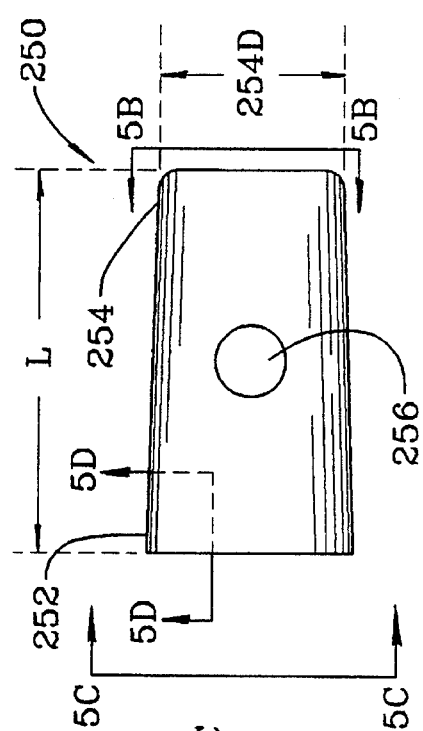
FIG. 5A is a side view of the nasal tip member of the second embodiment of the invention without the inflatable cuff attached thereto.
Figure 5C:
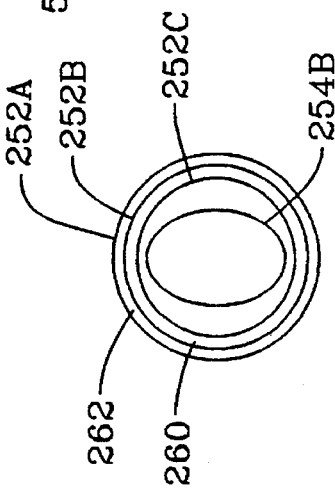
FIG. 5C is a proximal end view of the tip member shown in FIG. 5A.

Referring now to FIGS. 5A–5C, the preferred design of removable nasal tip 250 will now be discussed. FIG. 5A is a side view of tip 250. Tip 250 preferably has a length "L" in the range of about 0.5 to 1.0 inch, and more preferably about 0.75 inch. Tip 250 preferably has a maximum outer diameter at proximal end 252 of about 0.4 to 0.5 inch, and more preferably about 0.45 inch. The second, distal end 254 preferably has a maximum outer diameter in the range of about 0.3 to 0.5 inch, and more preferably about 0.4 inch. Aperture 256 is a hole through the sidewall of tip 250 midway along the length of tip 250, and has a diameter in the range of about 0.020 to about 0.150 inch, and more preferably about 0.125 inch. As shown, the tip sidewall is tapered to gradually decrease in diameter from proximal end 252 to distal end 254.

Referring now to FIG. 5B, a distal end view of tip 250 along lines 5B—5B of FIG. 5A, proximal end 252 of tip 250 has a constant outer diameter defining a substantially circular cross-section. The outer diameter of the proximal end 254, however, defines a substantially oval cross-section indicated at 254A. As stated above, the major outer diameter 254D of the second, oval end 254A, shown vertically oriented in FIG. 5B, preferably is about 0.4 inch. The minor outer diameter 254d of the distal oval end 254 preferably is about 0.3 inch when the major outer diameter 254D is about 0.4 inch. The open distal end of tip 250 also is shown in FIG. 5B at 254B. As shown, the major inner diameter 254E of the opening at the distal end of tip 250 is aligned with the major outer diameter of tip end 254, with the minor inner diameter 254e substantially perpendicular to the major diameters. Preferably, major inner diameter 254E is about 0.29 inch when major outer diameter 254D is about 0.4 inch, and minor inner diameter 254e is about 0.2 inch when minor outer diameter 254d is about 0.3 inch.

FIG. 5D is a partial side cross-section view of tip 250 taken along lines 5D—5D of FIG. 5A. As there shown, proximal end 252 of the tip 250 has a substantially cylindrical recess 260 extending distally from the proximal end face 262 of tip 250. Cylindrical recess 260 is configured and dimensioned to receive the distal end 228 of nasal member 222. Surface 252A defines the outer surface of the proximal end 252 of tip 250. Surface 252B is the inner surface of cylindrical recess 260, and surface 252C is the inner surface of the proximal end 252 of tip 250. As will be explained in further detail below, inner surface 252B may be provided with one or more ribs, pins or other protrusions 264 to enhance positive friction fit between tip 250 and nasal member 222. Protrusions 264 may be continuous or discontinuous about the circumference of the tip 250.

FIG. 5C is a proximal end view of tip 250 taken along lines 5C—5C of FIG. 5A showing end face 262 and the circular cross-section of the proximal end 252 of tip 250. As shown, surfaces 252A, 252B and 252C are substantially circular in diameter at the proximal tip section with recess 260 between surfaces 252B and 252C. Also visible in FIG. 5C is oval aperture 254B at the distal end of tip 250.

FIG. 5E is a partial cross-section view taken along lines 5E—5E of FIG. 4, showing the proximal tip section 252 mounted onto nasal member 222 in accordance with a preferred friction fit construction. As shown, distal end 228 of nasal member 222 preferably has a reduced diameter section 270 extending distally therefrom configured to be inserted into cylindrical recess section 260 of tip member 250. Reduced diameter section 270 is friction fit within the cylindrical recess 260 of tip member 250 to hold tip 250 onto nasal member 222, and may include an annular recess 272 configured and dimensioned to receive annular ridge 264 on surface 252B to securely removably connect tip 250 to nasal member 222. As will be appreciated, given the substantially circular cross-section of nasal member end 228 and reduced diameter section 270, as well as the substantially circular cross-section of tip member proximal end 252 engaged therewith, tip 250 is rotatable relative to nasal member 222.

Figure 12:
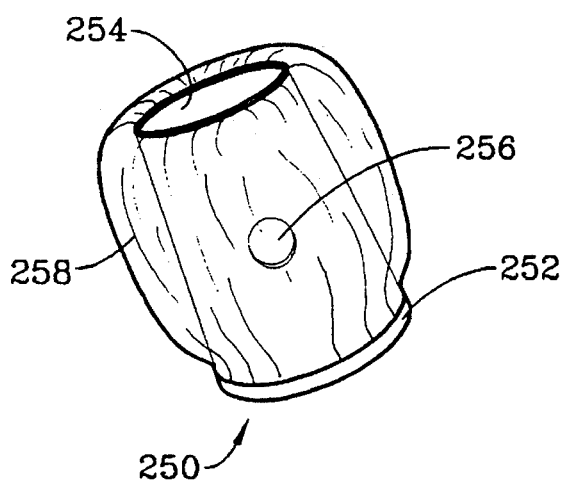
FIG. 12 is a perspective view of the nasal tip member of the second embodiment of the invention with an inflatable cuff attached thereto, such as by the steps illustrated in FIGS. 10–11.

FIGS. 5A–5E illustrate tip 250 without inflatable cuff 258. It should be understood that in the preferred embodiment tip member 250 includes inflatable cuff 258, as shown in FIGS. 4 and 12.

In use, tip members 250 are mounted to nasal members 222 which, in turn, are connected to nasal tubes 16, 18, connector 14 and primary air supply tube 12. The device is comfortably secured to the user's head with headband 24, and tips 250 are inserted into the patient's nares. Strap 42 may be inserted through strap-receiving members 38, 40 and attached to headband 24 to provide additional support for the device. The source of pressurized air (not shown) is activated to supply pressurized air to the device. The air source may be of the traditional continuous pressure type which provides a constant source of pressure to tip members 250, i.e., nCPAP treatment. Alternatively, the air source may be of the type which provides multiple levels of pressurized air, e.g., as used in BiPAP™ therapy. The pressurized air travels through the lumen of tip member 250 into the nares to effect the desired treatment. At the same time, pressurized air travels through aperture 256 to enter and inflate cuff 258, bringing cuff 258 into contact with the nares walls to hold the tip member in place. During exhalation the cuff remains inflated under pressure of exhaled gases and the exhaled gases are vented to atmosphere through vent holes 36.

Figure 13A:
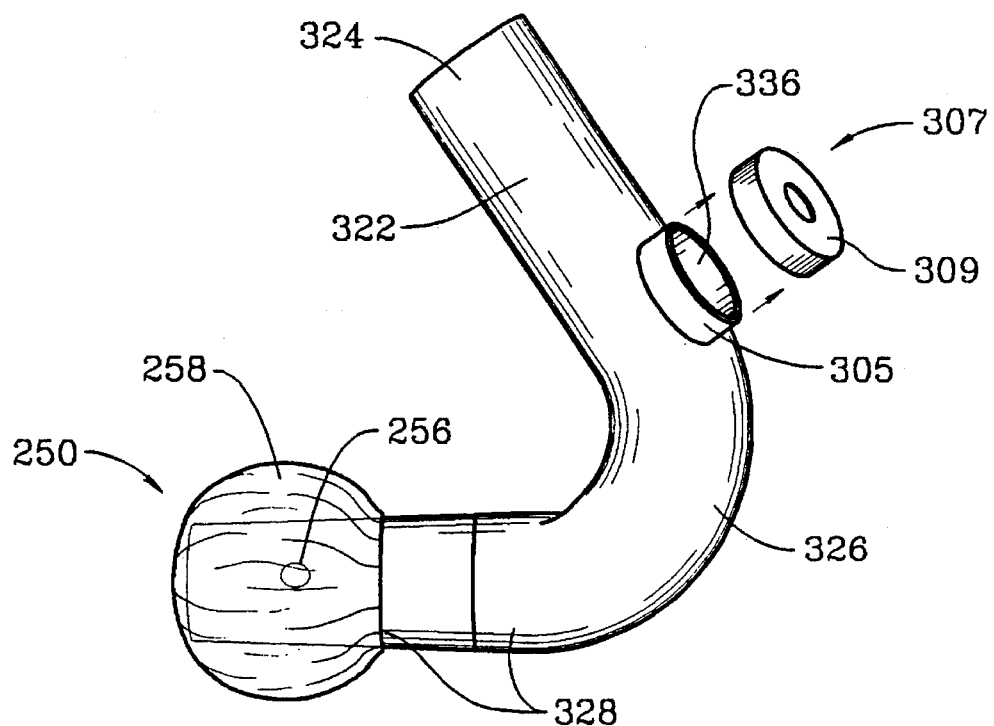
FIG. 13A is a perspective view of a nasal member similar to the embodiment shown in FIG. 4, incorporating a variable orifice in accordance with an alternative embodiment of the invention, showing the variable orifice cap spaced from the nasal member.
Figure 13B:
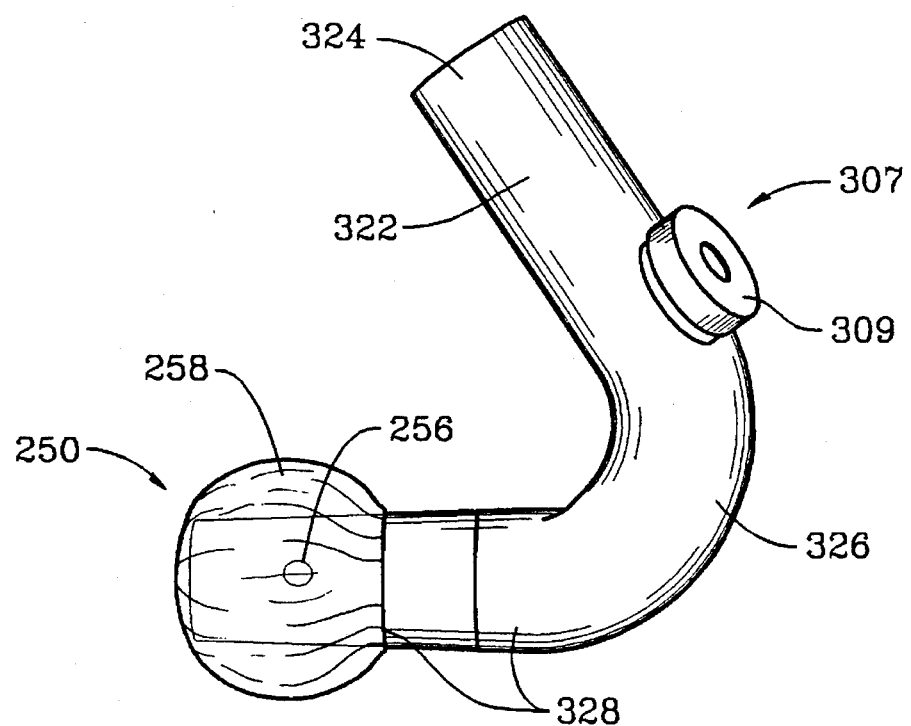
FIG. 13B is a perspective view of the alternative embodiment of the invention shown in FIG. 13A, shown with the variable orifice cap mounted to the nasal member.

A further alternative embodiment of the invention is shown in FIGS. 13A–13B and 14A–14D. FIG. 13A is a perspective view of a nasal member substantially as shown in FIG. 4 including a variable orifice aperture. Nasal member 322 has a proximal nasal tube receiving section 324, a curved body section 326 and a distal tip engaging end 328. A nasal tip section 250 with at least one aperture 256 and an inflatable cuff 258 is shown mounted to nasal member 322. As shown in FIG. 13A, aperture 336 in nasal member 322 is defined by a substantially cylindrical projecting wall 305. A variable orifice cap 307 is shown in FIG. 13A spaced from cylindrical wall 305. Variable orifice cap 307 is made of a flexible material such as latex rubber, and is formed so as to fit over and frictionally engage cylindrical wall 305, as shown in FIG. 13B. Cap 307 has an aperture defining surface 309.

Figure 14A:
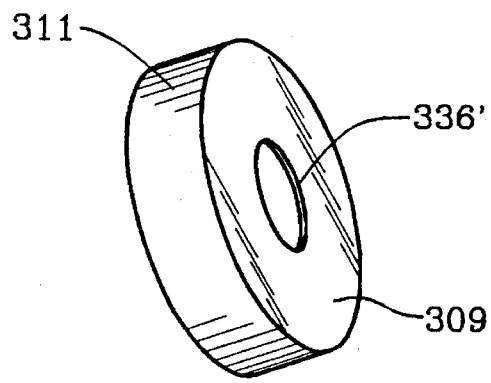
FIG. 14A is a perspective view of the variable orifice cap illustrating the orifice defining surface in the first, unexpanded condition to provide a first aperture diameter.
Figure 14B:
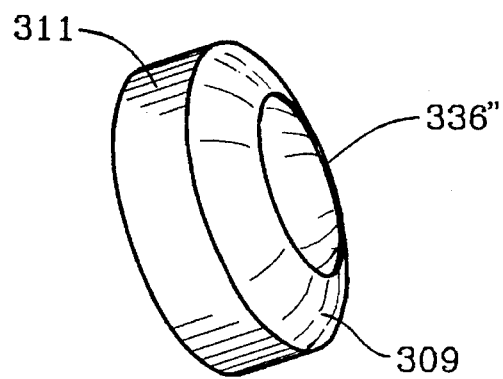
FIG. 14B is a perspective view of the variable orifice cap illustrating the orifice defining surface in the second, expanded condition to provide a second, enlarged aperture diameter.
Figure 14C:
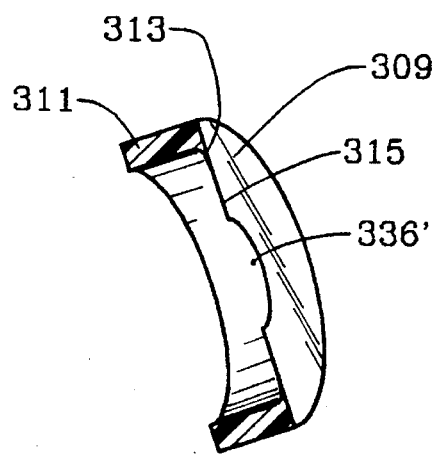
FIG. 14C is a sectional view, in perspective, of the variable orifice cap of FIG. 14A.
Figure 14D:
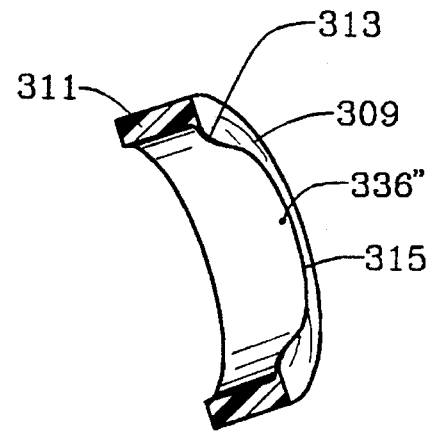
FIG. 14D is a sectional view, in perspective, of the variable orifice cap of FIG. 14B.

Referring now to FIGS. 14A–14D, variable orifice cap 307 is shown in greater detail. FIG. 14A is a perspective view of the variable orifice cap showing vertical side wall 311 and aperture defining surface 309. The variable orifice cap is shown in FIG. 14A in the first, unexpanded state defining aperture 336' having a first, reduced diameter. Referring now to FIG. 14B, aperture defining surface 309 is shown in a second, expanded state defining an expanded aperture 336" having a second diameter which is larger than the diameter of 336'. FIG. 14C is a perspective sectional view of the variable orifice cap of FIG. 14A shown in the unexpanded state. As shown, side walls 311 have a first thickness sufficient to give rigidity to the cap and frictionally engage projecting wall 305. As shown, aperture defining surface 309 is of substantially reduced thickness compared to side wall 311, and may taper from a first thickness at a point 313 adjacent side wall 311 to a very thin, flexible thickness 315 immediately adjacent aperture 336'. Referring now to FIG. 14D, a perspective section view of the variable orifice cap of FIG. 14B showing aperture defining surface 309 in the expanded state, the aperture defining surface 309 is expanded in the area adjacent the aperture to define larger expanded aperture 336". More particularly, the reduced thickness portion 315 of surface 309 stretches under pressure to expand the diameter of the aperture.

In use, the variable orifice cap is placed over and onto the projecting wall 305 of U-shaped nasal member and the nasal member is placed into the patient's nostrils in the usual manner. During inhalation the pressure at the orifice cap is at a minimum level and the aperture defining surface 309 is in the unexpanded state shown in FIGS. 13B and 14A, 14C. During exhalation the gas pressure at orifice cap 307 increases and exerts pressure upon orifice defining surface 309 to cause the surface to stretch and expand, creating expanded orifice 336" as shown in FIGS. 14B and 14D. The variable orifice cap is an improvement over fixed aperture devices because the first, unexpanded aperture allows efficient transfer of pressurized gas to the nares of the patient at relatively low pressure during inhalation. Conversely, during exhalation the gas pressure adjacent variable orifice cap 307 substantially increases and the increased pressure causes orifice defining surface 309 to stretch and expand the aperture to the larger diameter expanded state, which allows exhaled gas to exit the device through the aperture with less resistance than with a fixed orifice device. Advantageously, the variable orifice cap may be used with any form of positive nasal airway pressure therapy, e.g. nCPAP or BiPAP™ therapy.

Of course, numerous modifications and alterations to the variable orifice embodiment will occur to those skilled in the art. By way of example only, the stretchable orifice defining surface could be mounted to the nasal member in a variety of ways, such as be mounting the stretchable membrane directly to the surface of the nasal member, such as by gluing a latex rubber membrane defining the variable orifice to the inside surface of the nasal member over an aperture. Similarly, a substantially flat variable orifice defining member could be placed over aperture 336, with a substantially rigid open-centered cap placed over the orifice defining member and projecting wall 305 to capture the orifice defining member between the cap and wall 305. In addition, it will be understood that the variable aperture can be positioned at other locations than shown in FIGS. 13A and 13B, as long as the variable aperture is placed reasonably close to the patient's nares along the path of the gas supply to the nares. These and other modifications will occur to those skilled after learning of and practicing the invention.

The embodiments of the present invention permit previously unattainable adjustability which enhances patient comfort and, hence, compliance. By way of example only, in the embodiment illustrated in FIGS. 4–5D and 12 the rotatable tip member provides maximum adjustability and comfortable to the user. Because tip member 250 is rotatable relative to nasal member 222 the optimum position of the tapered oval distal end of the tip member within the nares can readily be found. Nasal members 222 preferably also are rotatably connected to nasal tubes 16, 18, such as by a rotational snap-fit connection similar to that shown in FIG. 5E for connecting the nasal tip member to the nasal member. The use of flexible nasal tubes 16, 18 further facilitates adjustment of the device to accommodate a variety of differently spaced nares, as required by patient physiology. Because tips 250 and nasal members 222 are rotatably connected to each other the relative rotational position of tip members 250 and nasal members 222 advantageously may be adjusted in combination with the spacing of nasal tubes 16, 18 to achieve the optimum configuration and orientation for patient comfort. The use of corrugated flexible tubing further facilitates spacing of the tip members and optimization of the vertical distance from nasal members 222 to connector 14 to further accommodate the physiological structure of the patient.

The embodiment of FIG. 3 similarly provides several degrees of flexibility of adjustment to accommodate a patient's physiological structure. While the embodiment of FIG. 3 lacks rotational adjustment of tip member 250 relative to nasal member 222, the remaining flexibility of the nasal members relative to each other and to connector 14 are believed to constitute a significant advance in the art, particularly in view of the tapered tip configuration and oval open end of the nasal member of FIG. 3. In addition, it will be understood that nasal member 122 of FIG. 3 may be rotatably connected to the nasal tubes, such as by a snap fit connection of the type illustrated in FIG. 5E.

Because tip member 250 is removable from nasal member 222 the second embodiment is well suited to providing disposable tip members for hygienic reasons. Similarly, in the first embodiment of FIG. 3 the entire nasal member could be disposable. Alternatively, it is contemplated that the tip members could be washed and reused several times and replaced only infrequently.

Figure 6:
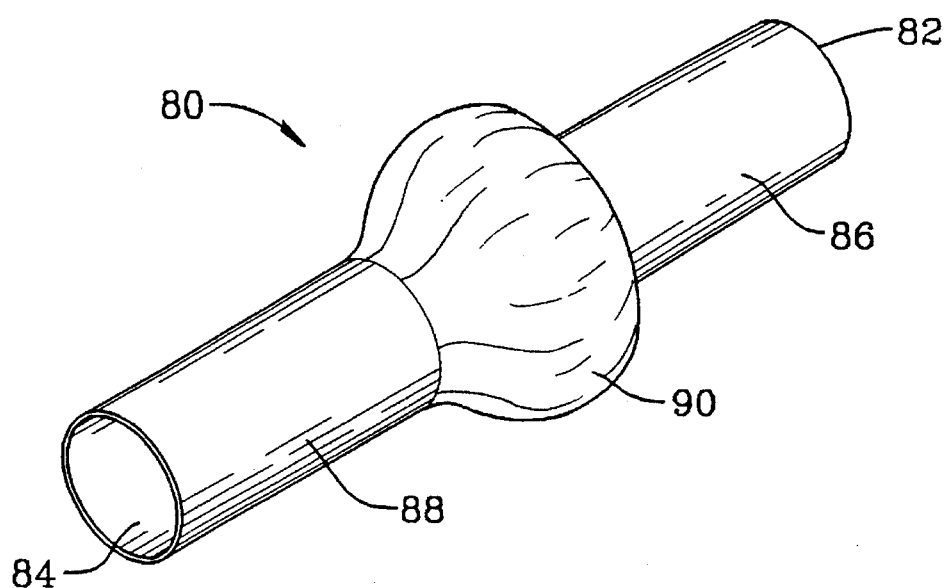
FIG. 6 is a perspective view of a mandrel useful for fabricating the inflatable cuffs in accordance with a method of the present invention.
Figure 7:
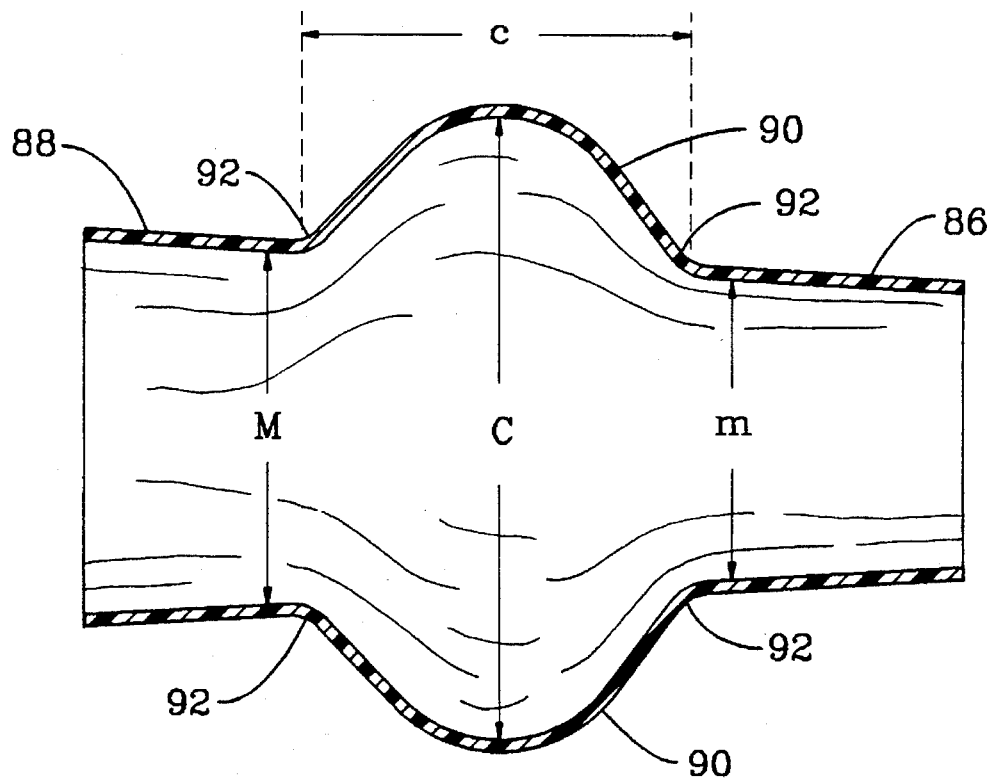
FIG. 7 is a side cross-section view of the mandrel of FIG. 6.

Referring to FIG. 6, a further aspect of the invention relates to the configuration and fabrication of the inflatable cuff and attachment thereof to the nasal tip. FIG. 6 is a perspective view of a mandrel 80 for fabricating an inflatable cuff in accordance with the invention. Mandrel 80 has a first and second open ends 82, 84, and first and second substantially cylindrical sections 86, 88, respectively. Mandrel 80 also has an enlarged hollow central section 90 joined at either side thereof to sections 86, 88. Mandrel 80 is substantially symmetrical about the longitudinal axis of sections 86, 88. Referring now to FIG. 7, a side cross-section view of mandrel 80, mandrel section 86 preferably has an inner diameter "m" of about 0.35 inches adjacent enlarged central section 90, which dimension is slightly smaller than the outer diameter of distal end 254 of nasal tip member 250 (see FIG. 4). Mandrel section 88 preferably has an inner diameter "M" adjacent enlarged section 90 of about 0.42 inches, i.e., slightly smaller than the outer diameter of a portion of nasal tip member 250 at a point proximal of the distal end 254. Central section 90 is connected to sections 86, 88 at smooth rounded transition zones 92 and has a maximum width "c" of about 0.40 inch and a maximum inner diameter C of about 0.80 inch.

Figure 8A:
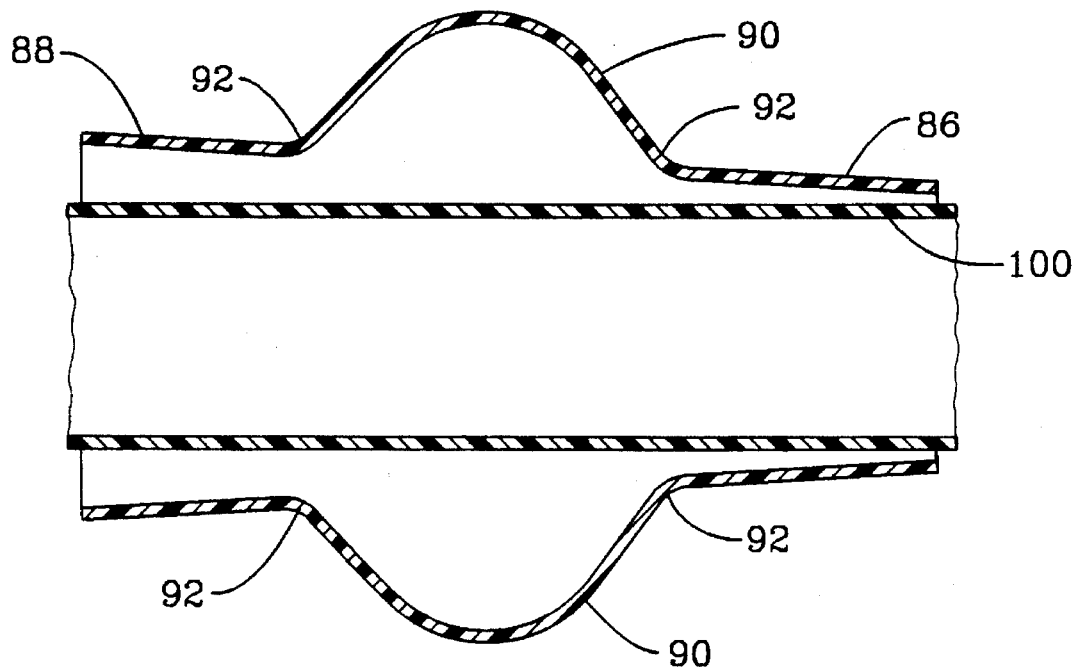
FIG. 8A is a side cross-section view of the mandrel shown of FIG. 6 illustrating a plastic tube disposed therein.
Figure 8B:
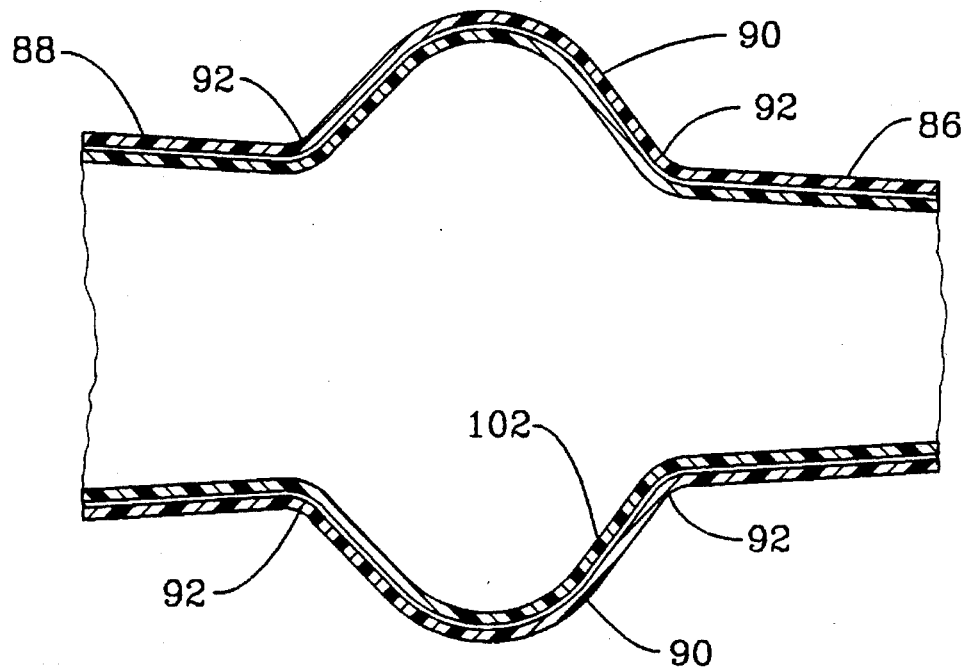
FIG. 8B is a side cross-section view of the mandrel shown in FIG. 8A after the plastic tube has been expanded.

The manner in which cuff 250 may be fabricated using mandrel 80 will now be explained with reference to FIGS. 8A and 8B. FIG. 8A is a cross-section view of mandrel 80 similar to FIG. 7 but with a thermoplastic tube 100 inserted therein. Tube 100 has an outer diameter on the order of but slightly smaller than the inner diameter of mandrel sections 86, 88 to facilitate insertion and removal of the tube. Preferably, tube 100 is a polyurethane plastic tube having a wall thickness on the order of about 2 to 6 mm and preferably about 4 mm. With tube 100 inserted into the mandrel, heat is applied to raise the temperature of at least at the central section of the tubing, or alternatively the entire tubing to a temperature above the glass transition temperature of the plastic but below the melting point of the plastic. As will be appreciated, heating the tubing to such a temperature allows the plastic to be deformed as desired without destroying the plastic material. Heating of the tubing may be accomplished in any number of ways, such as applying heat to the mandrel by passing hot air or liquid over the exterior of the mandrel or applying heat directly to the mandrel, e.g., by thermal conduction or electrical resistance, or by passing hot air or liquid through the mandrel and/or tube. Preferably, heat is applied to the exterior of the central section of the mandrel so as to heat that section of the adjacent tube. One end of the tube is sealed off before or during heating, and when the desired temperature is reached pressurized air or liquid is applied to the open end of the tube. The pressurized air or liquid applied to the tube also may be heated. Applying pressure to the heated tube in this manner causes the tube to expand to conform to the shape of the mandrel, as shown in FIG. 8B. In particular, the tube expands in the area adjacent the central section of the mandrel to form a bulbous region 102 of tubing connected to two substantially cylindrical tube sections. The bulbous region of the tubing conforms substantially to the shape of the mandrel center section. As will be appreciated, expanding the tube in this manner will cause the wall thickness of bulbous region 102 to thin out, reaching a minimum thickness at the maximum diameter "C" of the central section. Preferably, expanded bulbous region 102 of the tube 100 has a wall thickness of about 1 to 2 mm at the maximum diameter of the mandrel central section when the starting wall thickness of the tube is about 4 mm. After the bulbous region has been formed, the tubing and mandrel are cooled to room temperature, i.e., below the glass transition temperature of the plastic tubing, and the tubing is removed from the mandrel. Stretched bulbous region 102 is soft, flexible and relatively inelastic, and may readily be withdrawn from mandrel 80. Rounded transition zones 92 ensure that the expanded tube can be withdrawn without damage. As will be appreciated, mandrel 80 may be made of any material which will withstand heating to the desired temperature without undergoing substantial deformation. Glass and ceramic materials and metals such as stainless steel are contemplated and believed to be suitable to form mandrel 80.

Figure 9:
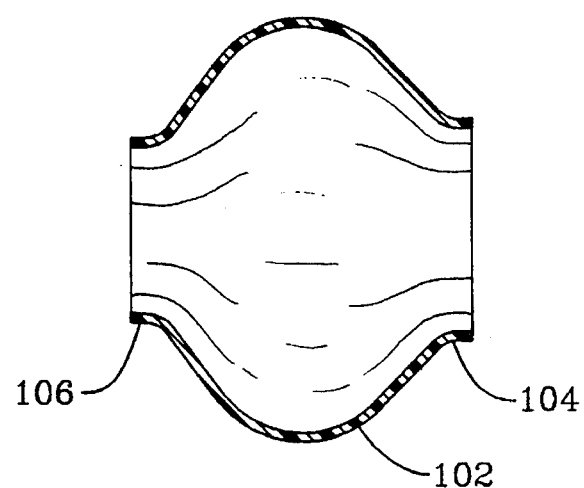
FIG. 9 is a side cross-section view of a portion of the expanded tube shown within the mandrel in FIG. 8B after the tube is removed from the mandrel and the central expanded section is cut therefrom.

After removal from the mandrel, bulbous section 102 is cut from the tubing to provide a cuff having an axial cross-section similar to that shown in FIG. 9. Because mandrel tube section 86 has an inner diameter slightly less than the outer diameter of distal end 254 of nasal tip member 250, lip 104 of the cuff also has a diameter slightly less than distal end 254. Similarly, lip 106 of bulbous section 102 corresponds to mandrel tube section 88 and has a diameter on the order of the diameter of an area of tip 250 proximate of tip end 254.

Figure 10:
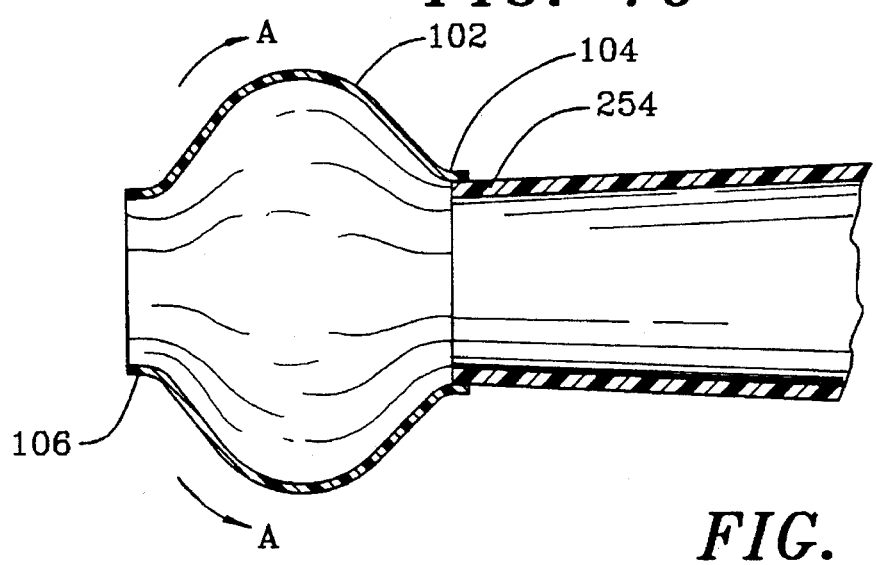
FIG. 10 is a side cross-section view of the expanded tube section shown in FIG. 9 attached at one end thereof to the distal end of the nasal tip member illustrated in FIGS. 5A–5D.

Referring now to FIG. 10, lip 104 is placed over distal tip 254 with expanded bulbous section 102 distal to the end of the nasal tip. Friction fit helps hold the lip 104 onto distal end 254, but it is preferred that an adhesive, cement or other suitable bonding compound be applied to join lip 104 to tip distal end 254. Suitable adhesives include epoxy resins, cyanoacrylates (such as Loctite Medical Grade Adhesives) and others. In one contemplated method a suitable plastic solvent adhesive is applied to join lip 104 of the bulbous section to distal tip 254. Bulbous section 102 is then everted in the direction of Arrows "A" from the position shown in FIG. 10 toward the proximal end 252 of tip member 250 in order to form a cuff surrounding at least a portion of the tip member (see FIG. 11). Lip 106 is bonded to a region of tip 250 proximal of distal tip 254 toward proximal end 252 in the same or similar manner as lip 104 is bonded to distal end 254, e.g., glue, cement or plastic solvent, to form cuff 258 surrounding and enclosing the nasal tip member, including aperture 256 (see FIG. 12). It is contemplated that a cuff member may be fabricated and attached to a nasal member of the type illustrated in FIG. 3 in a similar manner.

Figure 11:
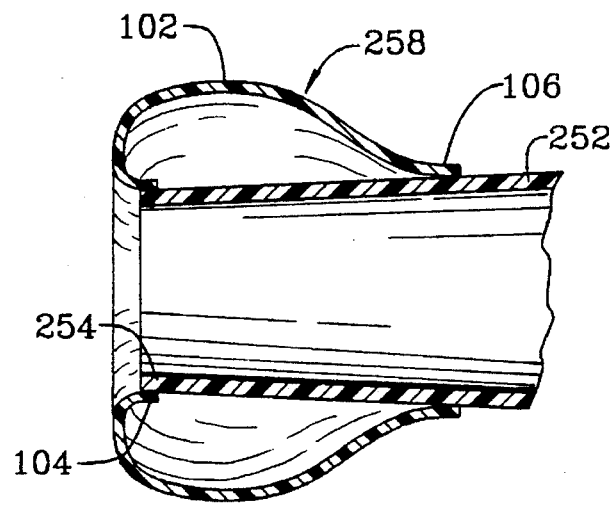
FIG. 11 is a side cross-section view of the nasal tip member shown in FIG. 10, illustrating the expanded tube section folded over the tip member and secured thereto proximal of the distal end thereof.

The attachment of cuff 258 to tip member 250 in the manner described in connection with FIGS. 10–12 provides a further significant advantage to the patient. By everting the bulbous section 102 after attachment to distal end 254, the resulting inflatable cuff 258 may and preferably is permitted to extend slightly beyond distal end 254, as illustrated in FIG. 12. Thus, when tip 250 is inserted into the nares and cuff 258 is inflated during use, as described above, cuff 258 effectively prevents tip member 250 from contacting the inner nares walls in any manner which might irritate the user and lead to a lack of compliance.

Device 10 may be fabricated in whole or in part from disposable or reusable plastics such as ABS plastic, polystyrene, polyethylene terathalate, polycarbonate, polyurethanes, polyesters, polypropylene, polyethylene, acrylics, etc. and may be fabricated by any suitable techniques such as blow or injection molding, extrusion, grinding cutting etc. The entire device may be disposable, or only parts of the instrument may be disposable. For example, all parts except tip members 250 might be relatively permanent with only tip members 250 being periodically replaced.

The foregoing description contains many specifics and numerous alternative structures and combinations will occur to those skilled in the art. For example, it is contemplated that the nasal tubes may be of flexible plastic without corrugations. In addition, it is contemplated that the nasal members could be supplied with pressurized air directly from a common, fixed plenum chamber without any connector hoses. Although such an arrangement does not provide as much flexibility in adjustment and is not preferred, the oval tip configuration and rotational adjustment thereof may provide sufficient advantage that these features alone achieve the purpose of providing a more comfortable nasal delivery system. It is further contemplated that an elastic material could be used to make the inflatable cuff, although the degree of elasticity at the operating pressures involved in the treatment of sleep apnea must be balanced so as not to irritate the patient's nares by expanding to such an extent that undue pressure is exerted against the nares walls. It is further contemplated that more than one aperture may be provided through the side wall of the nasal tip member to achieve substantially the same results. These and numerous other changes, variations and improvements will occur to those skilled in the art with practice of the invention claimed in the accompanying claims.

What is claimed is:

1. A device for treatment of sleep apnea comprising:

a pair of nasal members, at least a portion of each said nasal member defining a cannula having lumens and configured and dimensioned to fit within the nares of a patient, each said nasal member having a substantially oval cross-section at the open distal tip thereof, a substantially circular cross-section proximal of said distal tip, and a tapered body section between said oval cross-section and said circular cross-section, and at least one aperture through the sidewall of said tapered body section;

a pair of inflatable cuff members, each said cuff member surrounding at least a portion of said tapered body section of one of said nasal member and enclosing said aperture, the lumen of said nasal member and the interior said cuff in gaseous communication through said aperture; and a source of pressurized air connected to said nasal members to deliver pressurized air to the lumen of said nasal members.

2. The apparatus of claim 1 further comprising a pair of flexible nasal tubes each connected at a first end thereof to one of said nasal members and at a second end thereof to said source of pressurized air.

3. The apparatus of claim 1 wherein said nasal members include at least one vent hole.

4. The apparatus of claim 1 further comprising securing means for securing said apparatus relative to the head of a patient.

5. The apparatus of claim 4 wherein said securing means comprise a strap for engaging the apparatus and surrounding the head of a patient to secure the apparatus to the head of the patient.

6. The apparatus of claim 1 wherein said source of pressurized air is a substantially constant pressure source.

7. The apparatus of claim 1 wherein said source of pressurized air provides at least two different pressure conditions of air.

8. The apparatus of claim 2 wherein said nasal members are rotatably mounted to said flexible nasal tubes.

9. The apparatus of claim 8 wherein said nasal members are mounted to said nasal members by at least one rib in slot engagement.

10. The apparatus of claim 1 wherein said nasal member is made of a substantially rigid plastic material.

11. The apparatus of claim 1 wherein said inflatable cuff is made of a substantially inelastic material.

12. The apparatus of claim 11 wherein said inelastic material is plastic.

13. The apparatus of claim 12 wherein said inelastic plastic material is polyurethane.

14. A tip member for an apparatus for treating sleep apnea comprising a nasal tip member having a sidewall defining inner and outer surfaces and at least one aperture through said side wall, a first open end, a second open end and a body section between said first and second open ends, said first end having a substantially oval cross-section, said nasal tip member defining a cannula configured and dimensioned for insertion into a patient's nares, and an inflatable cuff secured to said outer surface off said tip member surrounding at least a portion of said tip member and enclosing said aperture, the interior space of said inflatable cuff in gaseous communication with the lumen of said nasal tip member through said aperture.

15. The tip member of claim 14 wherein said second open end has a substantially circular cross-section and said body section is tapered from said first end to said second end.

16. The tip member of claim 14 wherein said cuff extends slightly beyond said first open end in an inflated condition.

17. A method of treating sleep apnea comprising:
    providing an apparatus for treating sleep apnea including;
    (i) a pair of nasal tip members, each said tip member having a substantially oval first open end, a substantially circular second open end, and a tapered body section between said first and second ends, and at least one aperture through the sidewall of said tapered body section, each said tip member further including an inflatable cuff member surrounding at least a portion of said tapered body section and enclosing said aperture, each said nasal tip member defining a cannula configured and dimensioned for insertion into a patient's nares;
    (ii) a pair of nasal members rotatably mounted to said pair of nasal tip members at said second end of said tip members; and
    (iii) a source of pressurized air to simultaneously effect respiratory treatment to a patient and communicating with said nasal members to supply positive air pressure through said nasal members to said tip members;
    rotatably adjusting said nasal tip members relative to said nasal members;
    inserting said nasal tip members and inflatable cuffs into the nares of a patient to be treated;
    activating said source of pressurized air to supply air to said nasal tip members to inflate said cuffs under pressure of said pressurized air and cause said cuffs to contact the patient's nares to hold said nasal tip members within the patient's nares as treatment is effected with the pressurized air.

18. In an apparatus for the treatment of sleep disorders having at least one nasal member with a tip defining a lumen, at least a portion of the tip configured and dimensioned to be inserted into the nare of a patient, and a source of pressurized air connected to said at least one nasal member to supply positive air pressure to the lumen, the improvement comprising a variable orifice member spaced from the portion of said tip configured and dimensioned to be inserted into the nare of the patient, said variable orifice member in gaseous communication with the lumen and defining a variable orifice assuming a first position having a first diameter at a first gas pressure and a second, expanded position having a second diameter greater than said first diameter at a second, increased gas pressure.

19. The apparatus of claim 18 wherein the apparatus comprises a pair of nasal members each having a tip portion configured and dimensioned to be inserted into the nares of a patient.

20. The apparatus of claim 18 wherein said variable orifice member comprises a stretchable material having an aperture therethrough.

21. A method of treating sleep apnea comprising:
    providing an apparatus for treating sleep apnea including;
    (i) a pair of hollow nasal members having a body section and a tip configured and dimensioned to be inserted into the nares of a patient, each said nasal member including at least one variable aperture through the sidewall of said body section;
    (ii) a source of pressurized air communicating with said nasal members;
    inserting said tip members into the nares of a patient to be treated;
    activating said source of pressurized air to supply air to said hollow tip members to provide positive air pressure to the patient's nares, said variable aperture assuming a first diameter during inhalation by the patient and a second, enlarged diameter during exhalation by the patient.

22. The apparatus of claim 2 wherein said flexible tubes are expandable corrugated tubes, and whereby the relative position of said nasal members may be adjusted further by longitudinally expanding one or both of said expandable corrugated tubes.

23. A device for treatment of sleep apnea comprising:
    a pair of nasal members, at least a portion of each said nasal member defining a cannula configured and dimensioned to fit within the nares of a patient, each said nasal member having a first open end at the distal tip thereof, a second open end proximal of said distal tip, and a body section between said first and second ends defining a lumen between said first and second ends, and at least one aperture through the sidewall of said body section;
    a pair of inflatable cuff members, each said cuff member surrounding at least a portion of said body section of one of said nasal members and enclosing said aperture, the lumen of said nasal member and the interior of said cuff in gaseous communication through said aperture; and
    a source of pressurized air connected to said nasal members to deliver pressurized air to the lumen of said nasal members.

24. The apparatus according to claim 23 further comprising at least one vent hole in gaseous communication with the lumen of said nasal members.

25. A method of treating sleep apnea comprising:
    inserting a pair of nasal tip members into the nares of a patient to be treated, each said inserted nasal tip member having a first open end, a second open end, a body section between said first and second ends to define a lumen connecting said first and second open ends, and at least one aperture through the sidewall of said body section, each said inserted nasal tip member further including an inflatable cuff member surrounding at least a portion of said body section and enclosing said aperture;

activating a source of pressurized air connected to the lumen of said nasal tip members to supply air to said lumen to inflate said cuffs under pressure of said pressurized air and cause said cuffs to contact the patient's nares to hold said nasal tip members within the patient's nares.

26. A device for treatment of sleep apnea comprising:

a pair of nasal members, at least a portion of each said nasal member defining a cannula configured and dimensioned to fit within the nares of a patient, each said nasal member having a first open end at the distal tip thereof, a second open end proximal of said distal tip, and a body section between said first and second ends defining a lumen between said first and second ends, and at least one aperture through the sidewall of said body section;

a pair of inflatable cuff members, each said cuff member surrounding at least a portion of said body section of one of said nasal members and enclosing said aperture, the lumen of said nasal member and the interior of said cuff in gaseous communication through said aperture;

a pair of substantially U-shaped rigid tubes, each said nasal member rotatably mounted to one U-shaped tube;

a pair of flexible corrugated tubes, each corrugated tube connected to one said U-shaped tube opposite said nasal members; and a source of pressurized air connected to the ends of said flexible corrugated tubes opposite said U-shaped tubes to deliver pressurized air to the lumen of each nasal member through said U-shaped tubes.

27. The apparatus of claim 26 wherein each substantially rigid U-shaped tube includes at least one vent hole.

28. The apparatus of claim 27 wherein said vent hole comprises a variable orifice.

* * * * *